United States Patent [19]

Blair et al.

[11] Patent Number: 5,431,566
[45] Date of Patent: Jul. 11, 1995

[54] QUICK-COUPLED DENTAL HANDPIECE

[76] Inventors: Martin M. Blair, 14 Wilmington Dr., Dix Hills, N.Y. 11743; Mitchell N. Kay, Muttontown Rd., Muttontown, N.Y. 11545

[21] Appl. No.: 148,204

[22] Filed: Nov. 3, 1993

[51] Int. Cl.6 .................................................. A61C 1/08
[52] U.S. Cl. ................................................... 433/126
[58] Field of Search ............ 433/125, 126, 132, 82, 433/84

[56] References Cited

U.S. PATENT DOCUMENTS

| | | | |
|---|---|---|---|
| 4,075,761 | 2/1978 | Behne et al. | 433/126 |
| 4,080,737 | 3/1978 | Fleer | 433/126 |
| 4,117,597 | 10/1978 | Trist et al. | 433/132 |
| 4,318,695 | 3/1982 | Lieb et al. | 433/132 |
| 4,330,274 | 5/1982 | Friedman et al. | 433/29 |
| 4,330,279 | 5/1982 | Heil et al. | 433/126 |
| 4,334,863 | 6/1982 | Magid et al. | 433/29 |
| 4,375,964 | 3/1983 | Knopp et al. | 433/29 |
| 4,490,113 | 12/1984 | Kawada | 433/126 |
| 4,534,734 | 8/1985 | Lares | 433/126 |
| 4,975,058 | 12/1990 | Woodward | 433/29 |
| 5,033,960 | 7/1991 | Heil | 433/29 |
| 5,252,067 | 10/1993 | Kakimoto | 433/126 |

Primary Examiner—Cary E. O'Connor
Attorney, Agent, or Firm—Bauer & Schaffer

[57] ABSTRACT

The dental handpiece is removably coupled to the hose supplying air, water, etc. The coupling includes a bushing for interconnecting the conduits in the hose directly to the dental handpiece.

5 Claims, 2 Drawing Sheets

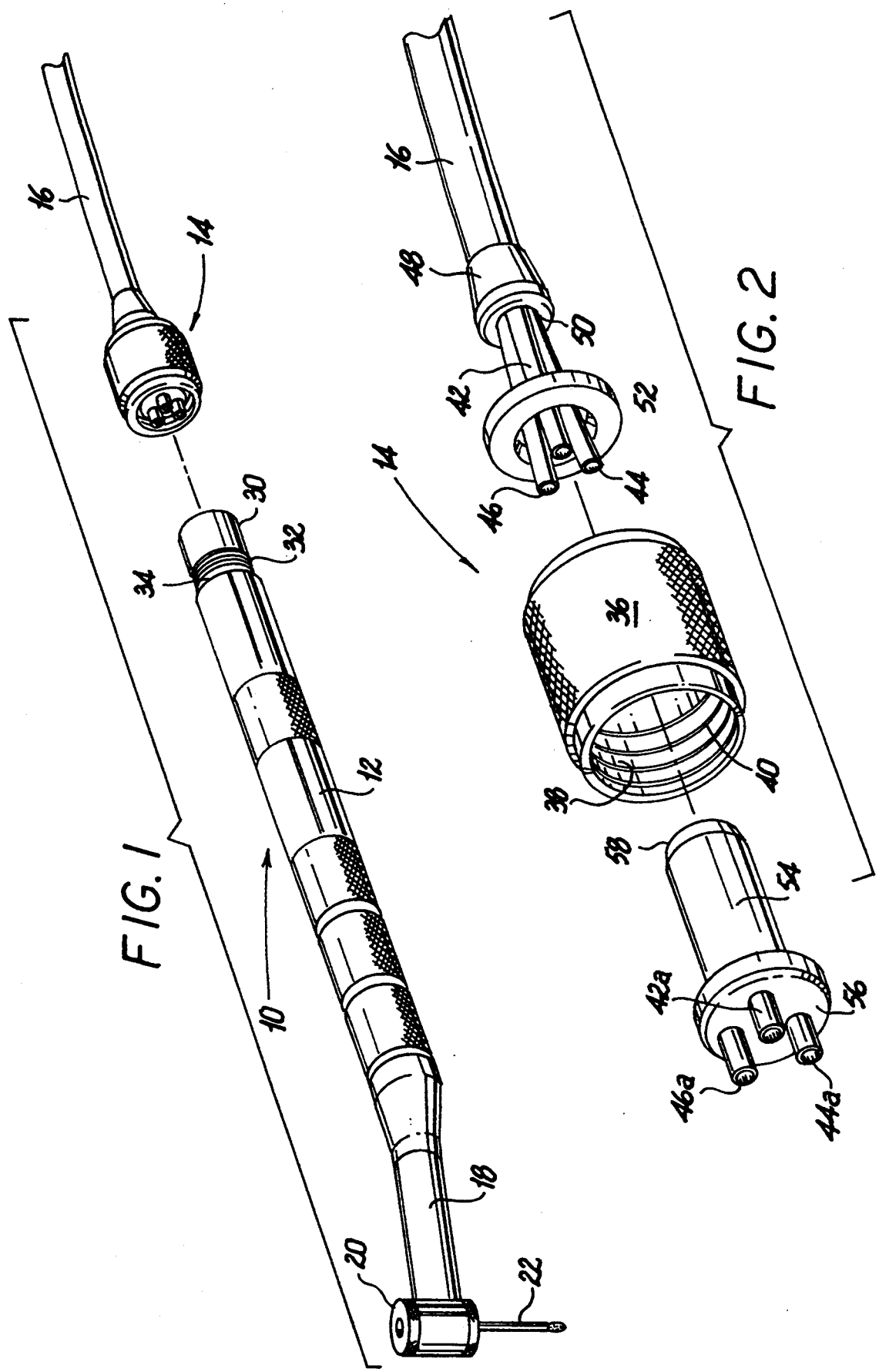

QUICK-COUPLED DENTAL HANDPIECE

BACKGROUND OF THE INVENTION

The present invention relates to the construction of dental handpieces and, in particular, to the provision of a handpiece assembly removably coupled to the supply hose.

In recent years, the epidemic of blood carried diseases, such as AIDS, has placed a severe problem in the hands of dentists and dental technicians. Cleaning and sterilizing dental instruments, especially the handpiece, using the old conventional methods are no longer safe and secure. To remove any apprehension that contaminated blood would remain on or in the handpiece being transferred from one patient to the next, it would be desirable to have individual handpieces assigned to and used only by single, individual patients.

Burs are made to be detachable from the handpiece in order to rapidly change to a different bur. Burs, however, are small and not the only part of the handpiece entering the mouth and coming into contact with blood and other contaminants. The head of the handpiece and part of the sheath enters the mouth as well.

Because the handpiece is manipulated with great force and is required to undergo twisting and rotative movements in the mouth, the sheath is normally connected to the supply hose in a permanent manner. Thus, even if it is possible to remove the bur, the equally contaminated sheath cannot easily be removed either for replacement or for cleaning and sterilization.

It is an object of the present invention to provide a handpiece in which the foregoing problem is obviated by constructing a handpiece assembly which is easily detachable from the supply hose.

Among the advantages of the present invention is the ability to provide each patient with his or her own assembly which the patient will take home and bring back on each visit to the dentist. The patient may then clean and sterilize the assembly so that the patient will have complete assurance that it will not be contaminated with another patient's blood.

In order to obtain a detachable handpiece, it is a further object of the present invention to provide an improved coupling by which the handpiece is held to the supply hose.

These objects and advantages, together with others, will be apparent from the following disclosure of the present invention.

SUMMARY OF THE INVENTION

According to the present invention the dental handpiece, normally provided with a hose having an array of conduits connected to sources of air, water and chip blower is detachably coupled to the rear end of the sheath to which the handpiece carrying the bur is attached. The detachable coupling includes within the sheath a conforming array of tubes or conduits which interfit with the corresponding members in the hose and a screw sleeve which interlocks the sheath and the hose causing the conduits to mate one within the other.

Preferably, the ends of the conduit in the hose and the ends of the ducts in the sheath fit together as plug and socket members whereby additional seal means will not normally be required.

Full details of the present invention are set forth in the following description and illustrated in the drawings appended hereto.

BRIEF DESCRIPTION OF THE DRAWINGS

In the drawings:

FIG. 1 is a perspective view of the dental handpiece and supply hose embodying the present invention;

FIG. 2 is an exploded view showing the coupling for securing the handpiece to the supply hose;

DESCRIPTION OF THE INVENTION

Figure 3:
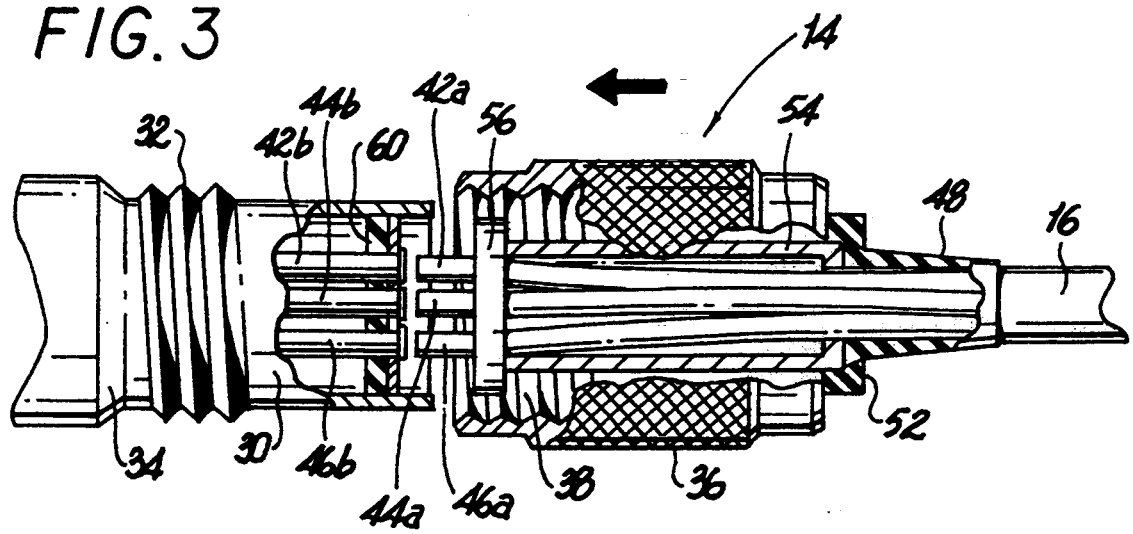
FIG. 3 is a partial sectional view in side elevation showing the coupling detached from the handpiece.

Briefly, as seen in FIG. 1, the handpiece assembly, generally referred to by the numeral 10, comprises a sheath 12 which, according to the present invention is detachably connected by a coupling generally depicted by the numeral 14 at its rear end to a supply hose 16. At the forward end of the sheath 12, there is an angularly disposed neck 18 at the free end of which is mounted the handpiece head 20 in which is held the bur 22.

The elements of the handpiece may be formed of metal and/or plastic as is conventional this art. The material from which the elements are formed is not critical to this invention although they should, of course, conform to the requirement of sanitation, strength, stability and sterilization common in this field. Further, the structure of the handpiece and the manner in which it is connected to the neck is also not critical here and may also follow any common or conventional form.

The coupling 14 as seen in FIG. 1 requires that the rear end of the sheath 12 be reduced in outer diameter to provide a smooth outer surface male element 30 provided with a screw thread 32 and terminating in a shoulder 34. The male element 30 is adapted to slide into a sleeve-like thimble female element 36 provided on its interior surface with a thread 38 matching that of the thread 32 on the sheath 12, and a smooth bore section 40 toward the rear.

The supply hose 16, in which is located three flexible conduits 42, 44 and 46 for water, air under pressure and chip blower, respectively, terminates in a ferrule 48, also provided with an internal thread 50. A large ring washer 52, fits over the protruding ends of the conduits 42, 44 and 46 abutting against the face of the ferrule 48. Passing through the thimble female element 36 is a hollow bushing 54 having a collared closure 56 at its forward end through which the three conduits 42, 44 and 46 pass and held fixedly in place. The collar 56 serves to prevent entry of dirt or contaminants into the hose when the handpiece is removed from it. Preferably the portions of the conduits extending out of the collared closure 56 are covered by thin metallic or rigid plastic sleeves, indicated by the reference numerals 42a, 44a and 46a respectively so as to form shape retaining plugs. The rear end of the bushing 54 is formed with a thread 58 which meshes with the thread 50 in the ferrule 48 so that the bushing may be secured to the ferrule holding the conduits firmly in place. As the bushing 54 passes through the thimble element 36, the thimble element will be able to freely slide between the ring 52 and the collar closure 54.

As illustrated in FIG. 3, the sheath 12 is itself provided with conforming conduits 42b, 44b and 46b; water, air and chip blower, arranged in and held securely by a bulkhead 60 in alignment with the corresponding conduits in supply hose 16. The conduits 42b, 44b and 46b have an inner diameter equal to or slightly larger than the outer diameter of the corresponding conduit sleeves 42a, 44a and 46a so that the two sets of conduit ends act like plug and sockets when the conduits in the supply hose fit within the conduits in the sheath and make a firm, secure connection without leakage.

Figure 4:
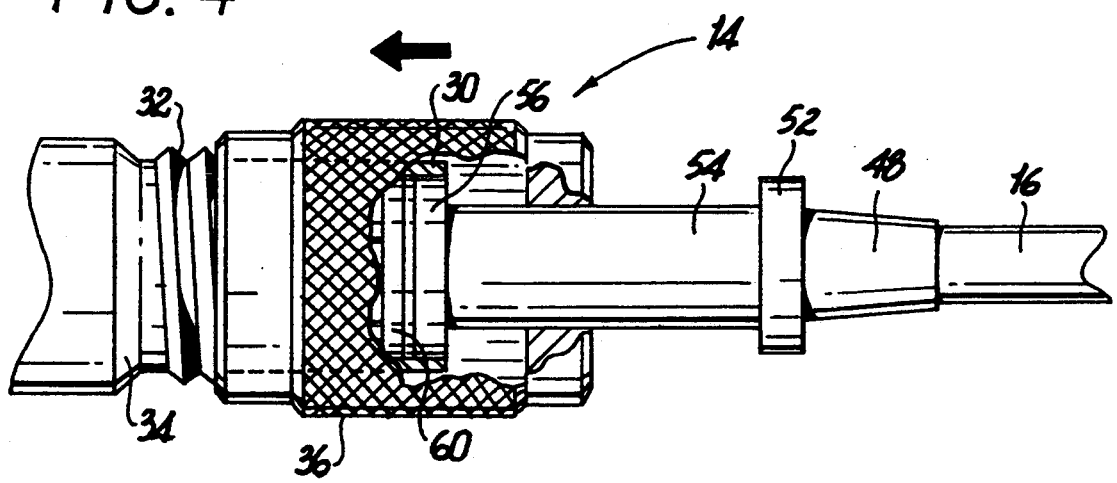
FIG. 4 is a view similar to FIG. 3 showing the coupling attached.
Figure 5:
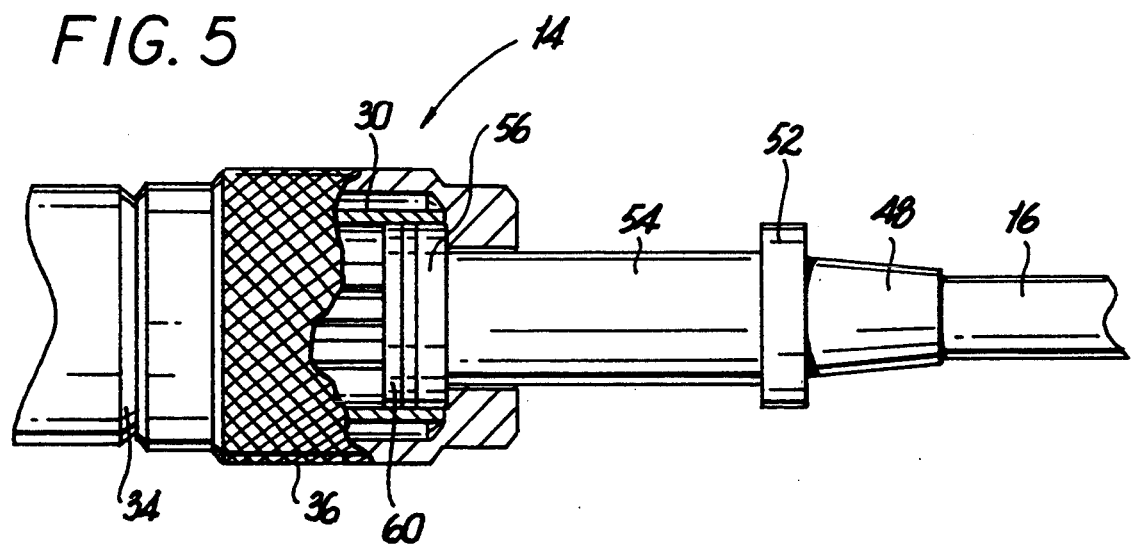
FIG. 5 is yet a similar view showing the coupling locked in place.

In connecting the sheath 12 to the supply hose the two are brought into axial alignment as seen in FIG. 3 and the conduit ends 42a, 44a and 46a pushed into the conduit ends 42b, 44b and 46b respectively. Simultaneously, the thimble sleeve is made to slide over the reduced diameter end of the sheath 12 and the threads 32 and 38 engaged as seen in FIG. 4. Upon fully threading the sleeve 36 over the end of the sheath 12, the collar closure 56 seats firmly against the bulkhead 60 being wedged in place by the nut-like head on the rear end of sleeve 36. Since the bushing 54 and its collar closure 56 are fixedly joined to the supply hose, the supply hose thus becomes fixedly coupled to the handpiece. Coupling is easy and can be swiftly accomplished. Similarly, decoupling or detachment is equally easy and swift by reversing the process.

By arranging the conduit 42, 44 and 46 in a standard array in both the supply hose and the sheath, interchangeable replacement and substitution of handpieces is no problem. Above all, the present construction does not modify the size, weight or outer arrangement of the handpiece. Therefore, the user or technician will not sense any change or deviation from the norm to which they have heretofore become accustomed.

After removing the handpiece, the instrument may be given to the patient, who is then responsible for its care. This responsibility on the part of the patient is desirable, since there can be no question of inadvertent misuse of the instrument or mix-up with those of other patients. A small package or box may be provided to house the instrument when not in use. Of course, the instrument should be washed, cleansed and sterilized, if desired, after each use. The patient will, of course, return to the dentist with the instrument for each visit.

The cost of providing handpieces for each patient is negligible in view of the very real and understandable risk of contacting diseases such as AIDS and would not present any real problem.

The handpiece is made preferably from brass coated with a silver finish. Other materials may be used.

Various modifications, changes and the like have been disclosed herein. Others will be apparent to those skilled in this art. Accordingly, the description herein is to be taken as illustrative only and not as limiting of the invention.

What is claimed is:

1. A dental drill assembly comprising a handpiece having a drillhead attached at one end and a hose attached at the other end, each of said handpiece and said hose being provided with conduits for separately carrying air, water and chip blower from respective sources, said handpiece being secured to said hose by a detachable coupling having passageways of the same number and in an identical array as the conduits in said hose and said handpiece, said coupling being interposed between said hose and said handpiece to securely interlock with said conduits in each of said hose and handpiece upon attachment of the handpiece to the hose to provide continuous connection between the conduits in said hose and the conduits in said handpiece for the air, water and chip blower, said coupling comprising a bushing in which said passageways are formed, said bushing being threaded at its rear end and secured to a mating thread formed at the end of said hose, said bushing having a collar at its forward end against which the other end of said handpiece is capable of abutment and through which said passageways protrude, said coupling having means for compressing the hose and handpiece together to secure said bushing therebetween.

2. The assembly according to claim 1, wherein said compression means comprises a thimble sleeve having an internal thread at its foward end and a reduced diameter at its rear end, said handpiece being formed with an exterior thread at its other end meshing with the thread of the thimble sleeve and said hose being provided with a ferrule at its forward end with which said reduced diameter hose wedges.

3. The assembly according to claim 2, wherein the end of said handpiece having the exterior thread is of reduced diameter such that the outer surface of said thimble sleeve makes a smooth transition to said handpiece.

4. The assembly according to claim 3, including a seal ring interposed between the end of the ferrule and the collar of said bushing.

5. The dental handpiece according to claim 1, wherein the conduit ends in said hose and handpiece, respectively, are dimensioned so as to fit one within the other in plug and socket connection on coupling said hose and handpiece together.

* * * * *